United States Patent [19]

Wagner et al.

[11] Patent Number: 4,836,984

[45] Date of Patent: Jun. 6, 1989

[54] DENTURES AND ALLOYS FOR USE IN SAME

[75] Inventors: Rudolf Wagner, Remchingen; Harry Schiwiora; Manfred Stümke, both of Pforzheim; Werner Groll, Alzenau-Hörstein, all of Fed. Rep. of Germany

[73] Assignee: Degussa Aktiengesellschaft, Frankfurt am Main, Fed. Rep. of Germany

[21] Appl. No.: 131,465

[22] Filed: Dec. 11, 1987

[30] Foreign Application Priority Data

Dec. 12, 1986 [DE] Fed. Rep. of Germany ....... 3642474

[51] Int. Cl.$^4$ ............................................... C22C 5/04
[52] U.S. Cl. ................................. 420/464; 420/465; 433/207
[58] Field of Search ................. 420/464, 465; 433/207

[56] References Cited

U.S. PATENT DOCUMENTS

| 4,451,639 | 5/1984 | Prasad | 420/464 |
| 4,551,302 | 11/1985 | Wagner et al. | 420/464 |
| 4,681,735 | 7/1987 | Groll et al. | 420/464 |

*Primary Examiner*—Robert McDowell
*Attorney, Agent, or Firm*—Cushman, Darby & Cushman

[57] ABSTRACT

Palladium alloys consisting of (a) 65 to 85% palladium, (b) 0 to 10% gold and/or 0 to 5% platinum, (c) 0.1 to 10% tin, (d) 1 to 10% gallium, (e) 1 to 12% copper, (f) 0.05 to 1.5% ruthenium and/or 0.05 to 0.7% rhenium as well as (g) 0.01 to 4% tungsten and/or 0.01 to 4% aluminum and/or 0.01 to 4% zinc are use to produce firmly seated and removable dentures. These alloys do not form oxide films when melted in air.

3 Claims, No Drawings

DENTURES AND ALLOYS FOR USE IN SAME

The present invention relates to the use of palladium alloys for producing fixed and removable dentures.

BACKGROUND OF THE INVENTION

German Patent Specification DE-PS 33 16 595 (corresponding to U.S. Pat. No. 4,551,302) discloses palladium alloys for producing fixed and removable dentures. The disclosure of this patent specification is incorporated herein by reference. The alloys described in that specification contain 65 to 85% palladium, 0 to 10% gold and/or 0 to 5% platinum, 0.1 to 10% tin, 1 to 10% gallium, 1 to 12% copper as well as 0.05 to 1.5% ruthenium and/or 0.05 to 0.7% rhenium. Thus, the base metal content can be up to 32% by weight.

When palladium alloys with such high base metal contents are melted in an oxidizing atmosphere, they occasionally tend to form a stable oxide film which floats on the liquid melt. The formation of such an oxide film brings about the accumulation and combustion of oxidizable alloy constituents. If the alloy is remelted several times, it can result in an undesired change of the alloy composition. Moreover, when a dental technician melts such alloy in an oxidizing atmosphere, he may not be able to see through the surface oxide layer and this is not able to perceive whether the alloy located under the oxide layer is sufficiently liquefied to be cast.

Another undesired phenomenon associated with the formation of an oxide film is the fact that the melting crucible occasionally does not discharge completely, so that slag residues remain on the crucible bottom. These oxide films occur in particular in the case of alloys which contain more than 10% base metals, depending on the type of base metals added.

SUMMARY OF THE INVENTION

The object of the present invention is to provide a palladium alloy for producing fired and removable dentures, which do not form oxide films in an oxidizing atmosphere during melting even at rather high base metal contents.

This object is achieved by a palladium alloy consisting of (a) 65 to 85% palladium, (b) 0 to 10% gold and/or 0 to 5% platinum, (c) 0.1 to 10% tin, (d) 1 to 10% gallium, (e) 1 to 12% copper, (f) 0.05 to 1.5% ruthenium and/or 0.05 to 0.7% rhenium as well as (g) 0.01 to 4% tungsten and/or 0.01 to 4% aluminum and/or 0.01 to 4% zinc, the combined percentages of these metals and unavoidable impurities being 100%.

DETAILED DESCRIPTION OF PREFERRED EMBODIMENTS

Alloys which have proven especially advantageous contain (a) 65 to 85% palladium, (b) 0 to 10% gold and/or 0 to 5% platinum, (c) 0.1 to 10% tin, (d) 1 to 10% gallium, (e) 1 to 12% copper, (f) 0.05 to 1.5% ruthenium and/or 0.05 to 0.7% rhenium and (g) 0.1 to 3% tungsten and/or 0.5 to 2% aluminum and/or 0.05 to 2% zinc.

Surprisingly, these alloys do not form an oxide layer on the melt when melted in an oxidizing atmosphere.

The following table shows the composition of such alloys.

| Pd | Au | Pt | Cu | Sn | Ga | Ru | Re | W | Al | Zn |
|---|---|---|---|---|---|---|---|---|---|---|
| 82.0 | | | 5.0 | 5.3 | 6.0 | | 0.5 | 1.0 | | 0.2 |
| 79.3 | 1.0 | 1.0 | 5.0 | 6.5 | 6.0 | 0.8 | | 0.3 | 0.1 | |
| 78.4 | | | 9.5 | 1.0 | 9.6 | 0.6 | 0.2 | 0.5 | 0.2 | |
| 77.7 | | | 9.0 | 3.0 | 8.5 | 0.8 | | 0.6 | 0.4 | |
| 76.5 | 2.0 | | 11.3 | 1.9 | 7.2 | 0.8 | | 0.3 | | |
| 76.0 | 1.5 | 0.5 | 11.0 | 1.9 | 7.2 | 0.8 | | 0.7 | 0.2 | 0.2 |
| 76.2 | 1.5 | 0.5 | 11.0 | 1.9 | 7.2 | | 0.5 | 0.7 | | 0.5 |
| 71.0 | 2.5 | 1.5 | 10.0 | 9.0 | 2.5 | | 0.5 | 2.0 | 0.6 | 0.4 |
| 70.0 | 4.0 | 4.0 | 9.0 | 4.0 | 6.3 | 0.5 | 0.2 | 1.6 | 0.3 | 0.1 |

What is claimed is:

1. A palladium alloy containing (a) 65 to 85% palladium, (b) at least one member of the group consisting of 0 to 10% gold and 0 to 5% platinum, (c) 0.1 to 10% tin, (d) 1 to 10% gallium, (e) 1 to 12% copper and (f) at least one member of the group consisting of 0.05 to 1.5% ruthenium and 0.05 to 0.7% rhenium as well as (g) at least one member of the group consisting of 0.01 to 4% tungsten, 0.01 to 4% aluminum and 0.01 to 4% zinc, the combined percentages of these metals and unavoidable impurities being 100% and the proportion of said member of the group consisting of tungsten, aluminum and zinc being sufficient to prevent the formation of an oxide film on the alloy when melted in an oxidizing atmosphere.

2. A palladium alloy as set forth in claim 1 containing (a) 65 to 85% palladium, (b) at least one member of the group consisting of 0 to 10% gold and 0 to 5% platinum, (c) 0.1 to 10% tin, (d) 1 to 10% gallium, (e) 1 to 12% copper and (f) at least one member of the group consisting of 0.05 to 1.5% ruthenium and 0.05 to 0.7% rhenium, as well as (g) at least one member of the group consisting of 0.1 to 3% tungsten, 0.05 to 2% aluminum and 0.05 to 2% zinc, the combined percentages of these metals and unavoidable impurities being 100% and the proportion of said member of the group consisting of tungsten, aluminum and zinc being sufficient to prevent the formation of an oxide film on the alloy when melted in an oxidizing atmosphere.

3. Fixed and removable dentures comprising the alloy set forth in claim 1 or claim 2.

* * * * *